United States Patent [19]

Gould et al.

[11] Patent Number: 4,670,452
[45] Date of Patent: Jun. 2, 1987

[54] DIOXO DIBENZOPYRANS AND ANTI-ALLERGIC USE THEREOF

[75] Inventors: Kenneth J. Gould, Long Whatton; John L. Suschitzky, Loughborough, both of England

[73] Assignee: Fisons plc, Ipswich, England

[21] Appl. No.: 695,459

[22] Filed: Jan. 28, 1985

[30] Foreign Application Priority Data

Feb. 1, 1984 [GB] United Kingdom ................ 8402577

[51] Int. Cl.$^4$ ................ C07D 493/02; C07D 405/14; A61K 31/41; A61K 31/35
[52] U.S. Cl. .................................... 514/382; 514/455; 548/253; 549/382
[58] Field of Search .................. 548/253; 549/387; 514/382, 455

[56] References Cited

U.S. PATENT DOCUMENTS 3,718,668  2/1973  Cairns et al. .................. 549/384

FOREIGN PATENT DOCUMENTS 1230087  4/1971  United Kingdom .
1389827  4/1975  United Kingdom .

Primary Examiner—Glennon H. Hollrah
Assistant Examiner—D. B. Springer
Attorney, Agent, or Firm—Marshall, O'Toole, Gerstein, Murray & Bicknell

[57] ABSTRACT

There are provided benzopyrans of formula I

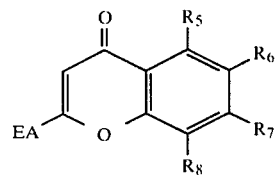

wherein
$R_6$ and $R_7$ together form the chain —CHOCH=$(A_1E_1)$—O— in which —O— is attached to $R_7$,
$R_5$ represents hydrogen,
$R_8$ represents propyl,
A represents a single bond,
$A_1$ represents a single bond, phenylene or $(CH_2)_m$,
m represents an integer from 1 to 10 inclusive,
E and $E_1$, which may be the same or different, independently represent —COOH, 5H-tetrazolyl, or $CONR_{24}R_{25}$, wherein $R_{24}$ and $R_{25}$, which may be the same or different, represent hydrogen or alkyl of $C_1$ to $C_6$;
provided that when $A_1$ represents a single bond, then $E_1$ represents 5H-tetrazolyl or $CONR_{24}R_{25}$, and their pharmaceutically acceptable salts, all of which are useful as anti-asthmatics.

7 Claims, No Drawings

DIOXO DIBENZOPYRANS AND ANTI-ALLERGIC USE THEREOF

This invention relates to new benzopyrans, processes for their production and compositions containing them.

Benzodipyran dicarboxylic acid derivative having anti-allergic properties are disclosed in U.K. Pat. No. 1230087. Certain benzodipyran derivatives substituted by tetrazolyl groups and having anti-allergic properties are disclosed in U.K. Pat. No. 1389827. We have now found a new group of benzopyran derivatives which have advantageous properties over compounds specifically disclosed in the above patent specifications.

According to the invention there are provided benzopyrans of formula I,

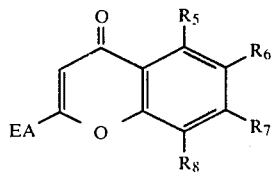

wherein
an adjacent pair of $R_5$, $R_6$, $R_7$ and $R_8$ represent the chain $-X-CR_{12}R_{13}-CR_{14}R_{15}-Y-$ in which the chain is substituted by $-A_1E_1$, X represents $CR_{10}R_{11}$ or a single bond, Y represents O, S or $CR_{16}R_{17}$, and (a) $R_{10}$ and $R_{12}$ together form a single bond or (b) $R_{12}$ and $R_{14}$ together form a single bond, or (c) $R_{10}$, $R_{12}$ and $R_{14}$ each represent hydrogen; and the remainder of $R_{10}$, $R_{11}$, $R_{12}$, $R_{13}$, $R_{14}$, $R_{15}$, $R_{16}$ and $R_{17}$, which may be the same or different, independently represent hydrogen, alkyl, $NR_{21}COR_{22}$, CN or $C_nH_xF_{(2n+1-x)}$; in addition, a geminal pair of $R_{10}$, $R_{11}$, $R_{12}$, $R_{13}$, $R_{14}$, $R_{15}$, $R_{16}$, and $R_{17}$ together with the carbon atom to which they are attached, may represent $C=O$ or $C=N-OR_{23}$; also a vicinal pair of $R_{11}$, $R_{13}$, $R_{15}$ and $R_{17}$, may form the chain $-CH=CH-CH=CH-$ which is substituted by $A_1E_1$, A and $A_1$, which may be the same or different, represent a single bond, $(CH_2)_m$ or arylene, n represents an integer from 1 to 10 inclusive, x represents 0 or an integer from 1 to 2n inclusive, m represents an integer from 1 to 10 inclusive, $R_{21}$, $R_{22}$, and $R_{23}$, which may be the same or different, independently represent hydrogen, alkyl or aryl;

the remainder of $R_5$, $R_6$, $R_7$ and $R_8$, which may be the same or different; each independently represent hydrogen, hydroxy, alkoxy, amino, halogen, nitro, cyano, alkyl, aryl or alkyl substituted by aryl, E and $E_1$, which may be the same or different, independently represent $-COOH$, or 5H-tetrazolyl, provided that when the chain $-X-CR_{12}R_{13}-CR_{14}R_{15}-Y-$ represents a chain $-CO-CR_{13}=CR_{15}-Y-$ in which Y is O or S and A and $A_1$ each represent a single bond, then Y is bonded to $R_7$, $R_5$ and $R_{13}$ each represent hydrogen, $R_8$ represents propyl and $R_{15}$ represents $E_1$, in which $E_1$ represents 5H-tetrazolyl or $CONR_{24}R_{25}$, wherein $R_{24}$ and $R_{25}$, which may be the same or different, represent hydrogen, alkyl or aryl; and pharmaceutically acceptable derivatives thereof.

According to the invention there is also provided a process for the production of a benzopyran of formula I, or a pharmaceutically acceptable derivative thereof, which comprises (a) cyclising a compound of formula II, or a suitable derivative thereof,

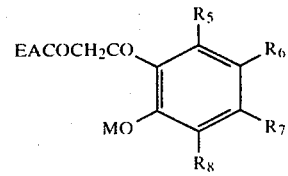

in which M represents a hydrogen atom or an alkali metal, and E, A, $R_5$, $R_6$, $R_7$ and $R_8$ are as defined above, (b) producing a compound of formula I, in which at least one of E and $E_1$ represents $-COOH$, by hydrolysing a compound of formula I in which the corresponding E, or $E_1$ represents a group hydrolysable to a $-COOH$ group, (c) producing a compound of formula I, in which at least one of E and $E_1$ represents 5-tetrazolyl,
by reacting a compound of formula I, in which the corresponding E or $E_1$ represents $-CN$, with an azide in a solvent which is inert under the reaction conditions, (d) producing a compound of formula I, in which $E_1$ represents $-CONR_{24}R_{25}$, by reacting a compound of formula I in which $E_1$ represents $-COL$, wherein L is a good leaving group, with a compound of formula III, $$R_{24}R_{25}NH \qquad III$$

in which $R_{24}$ and $R_{25}$ are as defined above, or (e) producing a compound of formula I, in which at least one of $R_{10}$, $R_{11}$, $R_{12}$, $R_{13}$, $R_{14}$, $R_{15}$, $R_{16}$ and $R_{17}$ represents $C_nH_xF_{(2n+1-x)}$,
by reacting a compound of formula I, or a derivative thereof, in which the corresponding $R_{10}$, $R_{11}$, $R_{12}$, $R_{13}$, $R_{14}$, $R_{15}$, $R_{16}$ or $R_{17}$ represents $L_1$,
wherein $L_1$ is a halogen atom,
with a compound $C_nH_xF_{(2n+1-x)}L_2$, in which n and x are as defined above and $L_2$ represents chlorine, bromine or iodine, and if necessary or desired converting the compound of formula I to a pharmaceutically acceptable derivative thereof or vice versa.

The cyclisation of process (a) may be carried out by heating, or under basic or neutral conditions. It is however preferred to carry out the cyclisation in the presence of an acid, e.g. gaseous or aqueous HCl, and in a solvent which is inert under the reaction conditions, e.g. ethanol or dioxan. The reaction may be carried out at from about 20° to 150° C. When E in the compound of formula I represents $-COOH$, E in the compound of formula II preferably represents a carboxylic acid ester, e.g. an ethyl or methyl ester.

Groups hydrolysable to a $-COOH$ group in process (b) include carboxylic acid amides, nitriles, carboxylic halides and preferably carboxylic acid esters. The conditions of the hydrolysis depend on the nature of the group, but may be carried out using conventional techniques, e.g. under mildly basic conditions, e.g. using sodium carbonate, sodium hydroxide, sodium bicarbonate; or under acidic conditions, e.g. hydrogen bromide in acetic acid. For carboxylic acid esters, we prefer to carry out the hydrolysis under basic conditions, e.g. using sodium hydroxide in an alkanol, e.g.

methanol. The hydrolysis may be carried out at a temperature of from about −5° to 120° C. depending on the compound and reagents used.

Suitable solvents which are inert under the reaction conditions of reaction (c) include those in which both reagents are soluble, e.g. N,N-dimethylformamide. Other solvents which may be mentioned include dimethylsulphoxide, tetrahydrofuran, diethylglycol and ethyl methyl glycol. The reaction is preferably carried out at a temperature of from about 20° to 130° C. for from about 1 to 20 hours. The azide used in the reaction is preferably ammonium or an alkali metal azide, e.g. sodium or lithium azide, but other azides, e.g. aluminium azide or the azides of nitrogen containing bases, e.g. mono-, di-, tri-, and tetra-methylammonium, anilinium, morpholinium and piperadinium azides, may also be used if desired. Where an azide other than that of an alkali metal is used, this azide may be prepared in the reaction mixture by double decomposition. The reaction may, if desired, be carried out in the presence of an electron acceptor, e.g. aluminium chloride, boron trifluoride, ethyl sulphonic acid or benzene sulphonic acid. As an alternative to the reaction conditions set out above the reaction may be carried out using hydrazoic acid (hydrogen azide) at a temperature of from about 20° to 150° C. in a suitable solvent, under greater than atmospheric pressure. When an azide other than hydrazoic acid is used, e.g. sodium azide, the product of the reaction will be the corresponding salt. This salt may be readily converted to the free acid by treatment with strong acid, e.g. hydrochloric acid.

The reaction of process (d) is preferably carried out in a solvent which is inert to the reaction conditions, e.g. diethyl ether, tetrahydrofuran, halogenated hydrocarbons such as dichloroethane and dichloromethane, or 1,4-dioxan. Good leaving groups that L may represent incude halide, especially chloride, and OCOCF$_3$. The reaction is preferably carried out at a temperature of from about 0° to 120° C. for from about 0.5 hours to 10 hours. The reaction is preferably carried out under anhydrous conditions under an inert atmosphere of, for example, nitrogen or argon. The reaction is preferably carried out in the presence of a proton acceptor, for example an excess of the compound of formula III or a non-nucleophilic proton acceptor, e.g. pyridine.

Process (e) may be carried out in a solvent which is inert under the reaction conditions, e.g. hexamethylphosphoric triamide or dimethylformamide. The reaction may be carried out on elevated temperature of from about 50° to 200° C., and may, if desired, be carried out in an inert atmosphere and under pressure. The reaction is preferably carried out in the presence of a copper catalyst (Ullmann reaction). We prefer the groups $L_1$ and $L_2$, which may be the same or different, to be selected from bromine and iodine.

Compounds of formula II and derivatives thereof, may be prepared by reacting a carbanion derived from the corresponding compound of formula IV, or a derivative thereof,

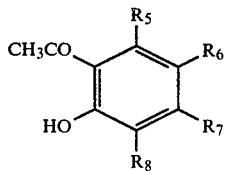

IV in which $R_5$, $R_6$, $R_7$ and $R_8$ are as first defined above, with a compound of formula V, $$ECOL_3 \qquad \text{V}$$

in which $L_3$ represents a good leaving group and E is as defined above.

The reaction is preferably carried out in a solvent which is inert to the reaction conditions, e.g. an alkanol such as ethanol, or dimethylformamide. Carbanions of the compound of formula IV may be formed by treating the compound of formula IV with a strong, non-nucleophilic base, for example a metal alkoxide such as potassium t-butoxide or sodium ethoxide, or a metal hydride, for example sodium hydride. Preferably an excess, for example four equivalents of base for each equivalent of the compound of formula IV is used. Good leaving groups that $L_3$ may represent include alkoxy, e.g. ethoxy. The reaction is preferably carried out at a temperature of from about 20° to 120° C. under an inert atmosphere and under anhydrous conditions.

The compounds of formula I in which at least one of E and $E_1$ represents a carboxylic ester may be made by processes analogous to those described under process (a) and, where appropriate, process (e).

The starting materials for process (c), i.e. compounds of formula I in which at least one of E and $E_1$ and $E_2$ represents —CN, may be prepared by reacting the compound of formula I in which the corresponding E or $E_1$ represents —CONH$_2$ with a dehydrating reagent. The reaction is preferably carried out using at least two molar equivalents of a dehydrating agent, e.g. POCl$_3$, per —CONH$_2$ group. The reaction may, if desired, be carried out in the presence of a proton acceptor, e.g. triethylamine. The reaction may be carried out in the presence of a solvent, e.g. N,N-dimethylformamide, dimethylsulphoxide, pyridine, benzene or hexamethyl phoshoric triamide, or an excess of the dehydrating agent may be used as the reaction medium. The reaction may be carried out at a temperature of from about 0° to 200° C. depending on the dehydrating agent used. When phosphorous oxychloride is used a temperature of from about 0° to 100° C. is preferred.

The compounds of formula I in which E or $E_1$ represents CONH$_2$ may be made in a conventional manner known per se from the corresponding carboxylic acid ester, e.g. by reaction of the ester with ammonia in an alkanol or dialkyl formamide solvent at a temperature of 0° to 120° C.

When L represents halide, the compounds of formula I in which E, or $E_1$ represents COL may be prepared by reacting the carboxylic acid with, for example, the appropriate thionyl halide or phosphoroyloxyhalide, under conventional conditions known per se. When L represents OCOCF$_3$, the mixed anhydride may be prepared from the corresponding carboxylic acid derivatives by conventional methods, e.g. by reaction with trifluoroacetic anhydride.

The compounds of formula III, IV and V are either known compounds or may be made from known compounds using for example techniques such as those described in the Examples.

The compounds of formula I and the intermediates therefor may be recovered from their reaction mixtures using conventional methods.

The process described above may produce the compound of formula I or a derivative thereof. It is also within the scope of this invention to treat any derivative so produced to liberate the free compound of formula I, or to convert one derivative into another.

Pharmaceutically acceptable derivatives of the compounds of formula I include pharmaceutically acceptable salts and, when any one of E or $E_1$ represents a carboxylic acid group, pharmaceuticaly acceptable esters or amides of the carboxylic acid groups.

Pharmaceutically acceptable salts of the compounds of formula I include ammonium, alkali metal (e.g. sodium, potassium and lithium) and alkaline earth metal (e.g. calcium or magnesium) salts, and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, or with simple monocyclic nitrogen heterocyclic compounds, e.g. piperidine or morpholine. Suitable esters include simple lower alkyl esters, e.g. the ethyl ester, esters derived from alcohols containing basic groups, e.g. di-lower alkyl amino substituted alkanols such as the beta-(diethylamino)ethyl ester, and acyloxy alkyl esters, e.g. a lower acyloxy-lower alkyl ester such as the pivaloyloxymethyl ester, or a bis-ester derived from a di-hydroxy compound, e.g. a di(hydroxy-lower alkyl)ester, e.g. the bis-2-oxapropan-1,3-diyl ester. The pharmaceutically acceptable acid addition salts of the basic esters, e.g. the hydrochloride, the hydrobromide, the oxalate, the maleate or the fumarate salts may also be used. The esters (when a —COOH group is present) may be made by conventionl techniques, e.g. esterification or transesterification. The amides (when a —COOH group is present) may be, for example, unsubstituted or mono- or di- C 1 to 6 alkyl amides and may be made by conventional techniques, e.g. reaction of an ester of the corresponding acid with ammonia or an appropriate amine.

The compounds of formula I and pharmaceutically acceptable salts, and, when E or $E_1$ is a —COOH group, pharmaceutically acceptable esters and amides thereof are useful because they possess pharmacological activity in animals; in particular they are useful because they inhibit the release and/or action of pharmacological mediators which result from the in vivo combination of certain types of antibody and specific antigen, e.g. the combination of reaginic antibody with specific antigen (see Example 27 of British Patent Specification No 1,292,601). The new compounds have also been found to interfere with reflex pathways in experimental animals and man, and in particular those reflexes associated with lung function. In man, both subjective and objective changes which result from the inhalation of specific antigen by sensitised subjects are inhibited by prior administration of the new compounds. Thus the new compounds are indicated for use in the treatment of reversible airway obstruction and/or to prevent the secretion of excess mucus. The new compounds are thus indicated for the treatment of allergic asthma, so-called "intrinsic" asthma (in which no sensitivity to extrinsic antigen can be demonstrated), bronchitis, coughs and the nasal and bronchial obstructions associated with common colds. The new compounds may also be of value in the treatment of other conditions in which antigen-antibody reactions or excess mucus secretion are responsible for, or are an adjunct to, disease, for example, hay fever; certain eye conditions, e.g. trachoma; alimentary allergy, e.g. urticaria and atopic eczema; and gastrointestinal conditions, for example gastrointestinal allergy, especially in children, e.g. milk allergy, or ulcerative colitis.

For the above mentioned uses the doses administered will, of course, vary with the compound employed, the mode of administration and the treatment desired. However, in general, satisfactory results are obtained when the compounds are administered at the dosage of from 0.001 to 50 mg per kg of animal body weight in the test set out in Example 27 of British Patent Specification No 1,292,601. For man the indicated total daily dosage is in the range of from 0.01 mg to 1,000 mg, preferably from 0.01 mg to 200 mg and more preferably from 1 mg to 60 mg, which may be administered in divided doses from 1 to 6 times a day or in sustained release form. Thus unit dosage forms suitable for administration (by inhalation or oesophageally) comprise from 0.01 mg to 50 mg, preferably 0.01 mg to 20 mg, and more preferably from 0.01 mg to 10 mg, of the compound preferably admixed with a solid or liquid pharmaceutically acceptable diluent, carrier or adjuvant.

The compounds of formula I, and pharmaceutically acceptable salts, and, when E or $E_1$ is a —COOH group, pharmaceutically acceptable esters and amides thereof, have the advantage that they are more efficacious in certain pharmacological models, or are longer acting than compounds of similar structure to the compounds of formula I. Furthermore the compounds of formula I, and pharmaceutically acceptable salts, and, when E or $E_1$ is a —COOH group, pharmaceutically acceptable esters and amides thereof, are advantageous in that they are more efficacious in interfering with reflex pathways and in inhibiting the secretion of mucus than are compounds of similar structure to the compounds of formula I.

According to the invention there is also provided the use of compounds of formula I to make a pharmaceutical formulation for the treatment of asthma.

$R_5$, $R_6$, $R_7$, $R_8$, $R_{10}$, $R_{11}$, $R_{12}$, $R_{13}$, $R_{14}$, $R_{15}$, $R_{16}$, $R_{17}$, $R_{21}$, $R_{22}$, $R_{23}$, $R_{24}$ and $R_{25}$ when they represent alkyl preferably represent alkyl C1 to 8, more preferably alkyl C1 to 6, for example methyl, ethyl or propyl.

When one or more of $R_5$, $R_6$, $R_7$, $R_8$, $R_{21}$, $R_{22}$, $R_{23}$, $R_{24}$ or $R_{25}$ represents aryl, preferred groups include heteroaryl groups, e.g. pyridinyl, quinolinyl and isoquonolinyl, as well as homoaryl groups. Homoaryl groups include phenyl, naphthyl, anthracenyl and phenanthryl. The aryl groups may be substituted by one or more of alkoxy, e.g. ethoxy, methoxy; halogen, e.g. chlorine, bromine, iodine, nitro or nitrile. We particularly prefer compounds in which aryl represents phenyl.

The chain —X—$CR_{12}R_{13}$—$CR_{14}R_{15}$— Y— may be formed between any adjacent pair of $R_5$, $R_6$, $R_7$ and $R_8$. However, we prefer those compounds in which the chain is formed between $R_6$ and $R_7$, particularly those compounds in which —X— is bonded to $R_6$ and —Y— is bonded to $R_7$.

Chains —X—$CR_{12}R_{13}$—$CR_{14}R_{15}$—Y— that may be specifically mentioned include:
—COCH=C($E_1$)—O— in which $E_1$ represents 5-tetrazolyl or $CONR_{24}R_{25}$;
COCH=C($C_6H_4$COOH)—O—;
COCH=C(($CH_2$)$_m$COOH)—O—;
$COCR_{13}$=$CR_{15}$—O—, in which $R_{13}$ and $R_{15}$ together form the chain —CH=CH—CH=CH—, the chain —CH=CH—CH=CH— being substituted by COOH;
—$CH_2CH_2$CH(COOH)—O—;

—$CH_2CH(COOH)CH_2CH_2$—;
—$CH_2CH_2CH(COOH)CH_2$—;
—$C(=NOR_{23})$—$CH=C(COOH)$—$O$—
—$CH=C(COOH)$—$CO$—$S$—; and
—$CR_{13}=CR_{15}$—$Y$—, in which one of $R_{13}$ and $R_{15}$ represents —COOH and the other represents hydrogen and Y represents O or S.

Halogens that $R_5$, $R_6$, $R_7$ or $R_8$ may represent include fluorine, bromine and iodine.

We prefer compounds of formula I in which $R_5$ represents hydrogen, hydroxy or alkoxy C1 to 6.

We prefer compounds of formula I in which $R_8$ represents alkyl C1 to 6, in particular propyl.

When one or more of $R_{10}$, $R_{11}$, $R_{12}$, $R_{13}$, $R_{14}$, $R_{15}$, $R_{16}$ or $R_{17}$ represents $C_nH_xF_{(2n+1-x)}$, n is preferably an integer from 1 to 6 inclusive, more preferably from 1 to 4 inclusive. We prefer compounds in which y is a larger integer than x. Particular groups that $C_nH_xF_{(2n+1-x)}$ may represent include those in which x is zero, for example $CF_3$, $C_2F_5$ and $C_3F_7$. Other groups that may be mentioned include $CHF_2$ and $CH_2CF_3$.

When a geminal pair of $R_{10}$, $R_{11}$, $R_{12}$, $R_{13}$, $R_{14}$, $R_{15}$, $R_{16}$ and $R_{17}$ together with the carbon atom to which they are attached represents C=O, we prefer either the pair $R_{10}$ and $R_{11}$ or the pair $R_{14}$ and $R_{15}$ together with the respective carbon atom to which they are attached to represent C=O. We particularly prefer compounds of formula I in which X represents C=O.

We prefer compounds of formula I in which $NR_{21}COR_{22}$ represents $NHCOR_{22}$.

We prefer compounds of formula I in which X represents C=N—$OR_{23}$.

When a vicinal pair of $R_{11}$, $R_{13}$, $R_{15}$ and $R_{17}$, form the chain —CH=CH— CH=CH— which is substituted by $A_1E_1$, the corresponding vicinal pair of $R_{10}$, $R_{12}$, $R_{14}$ and $R_{16}$ preferably represents a single bond, such that the chain —CH=CH— CH=CH— and the carbon atoms to which it is attached forms a six-membered carbocyclic aromatic ring. We prefer compounds in which the chain is connected between $R_{13}$ and $R_{15}$. We further prefer the chain —CH=CH—CH=CH— to be substituted by a group $E_1$, preferably COOH.

When A or $A_1$ represents arylene, arylene groups that may be mentioned include hetero- as well as homoarylene groups. Heteroarylene groups include 2,3-, 2,4-, 2,5- and 2,6-pyridinyl; 2,3-, 2,4-, 2,5-, 2,6- and 2,7-quinolinyl and 1,3-, 1,4-, 1,5-, 1,6- and 1,7-isoquinoliny. Homoarylene groups that A and $A_1$ may represent include 1,2-, 1,3- and 1,4- phenylene and 1,2-, 1,3-, 1,4-, 1,5-, 1,6- and 1,7-naphthalene. The arylene group may be substituted by one or more of alkoxy, e.g. ethoxy, methoxy; halogen, e.g. chlorine, bromine or iodine; nitro or nitrile. We particularly prefer compounds of formula I in which $A_1$ represents phenylene.

We prefer compounds in which A represents a single bond.

We prefer compounds of formula I in which m is an integer from 1 to 6 inclusive, preferably from 1 to 4 inclusive, e.g. 1, 2 or 3.

We prefer compounds of formula I in which E represents —COOH.

We prefer compounds of formula I which bear a single group $E_1$. We particularly prefer compounds in which one of $R_{13}$ or $R_{15}$ represents $E_1$, particularly —COOH.

As a preferred group of compounds we provide the compounds of formula I in which
an adjacent pair of $R_5$, $R_6$, $R_7$ and $R_8$ represents the chain —CO—$CR_{12}R_{13}CR_{14}R_{15}$—O—,
$R_{12}$ and $R_{14}$ together form a single bond,
one of $R_{13}$ and $R_{15}$ represents $A_1E_1$ and the other represents hydrogen, or $R_{13}$ and $R_{15}$ together form a chain —CH=CH—CH=CH—, the chain being substituted by $A_1E_1$,
A represents a single bond,
$A_1$ represents a single bond, phenylene or $(CH_2)_m$ and E, $E_1$, the remainder of $R_5$, $R_6$, $R_7$, $R_8$, m and the provisos are as defined above, and pharmaceutically acceptable derivatives thereof.

As a first specific group of compounds, we provide compounds of formula I in which
$R_6$ and $R_7$ together form the chain —COCH=$CE_1$—O—, in which —O— is attached to $R_7$.
$R_5$ represents hydrogen,
$R_8$ represents propyl,
A represents a single bond,
E represents —COOH or a 5H-tetrazolyl group,
$E_1$ represents —$CONR_{24}R_{25}$ or a 5H-tetrazolyl group
$R_{24}$ and $R_{25}$, which may be the same or different represent hydrogen or alkyl C1 to 6, and pharmaceutically acceptable derivatives thereof.

As a second specific group of compounds we provide compounds of formula I in which
an adjacent pair of $R_5$, $R_6$, $R_7$, and $R_8$ represents the chain —COCH=C($A_{11 E}$)—O—,
A represents a single bond,
$A_1$ represents phenylene,
E and $E_1$ each represent —COOH,
the remainder of $R_5$, $R_6$, $R_7$ and $R_8$ represent hydrogen or alkyl C1 to 6, and pharmaceutically acceptable derivatives thereof.

As a further group of preferred compounds, we provide the compounds of formula I in which
an adjacent pair of $R_5$, $R_6$, $R_7$ and $R_8$ represents the chain —$CHR_{10}$—$CHR_{12}$—$CHR_{14}$—Y—,
Y represents O or —$CHR_{16}$,
one of $R_{10}$, $R_{12}$, $R_{14}$ and $R_{16}$ represents —COOH and the remainder represent hydrogen,
A represents a single bond,
E represents —COOH,
the remainder of $R_5$, $R_6$, $R_7$ and $R_8$ which may be the same or different, independently represent hydrogen or alkyl C1 to 6, and pharmaceutically acceptable derivatives thereof.

As a goup of preferred compounds we also provide the compounds of formula I in which
an adjacent pair of $R_5$, $R_6$, $R_7$ and $R_8$ represents $CR_{13}=CR_{15}$—Y—,
wherein one of $R_{13}$ and $R_{15}$ represents COOH and the other represents hydrogen,
Y represents O, or S,
$R_{20}$ represents hydrogen or alkyl C1 to 6,
A represents a single bond,
E represents COOH, and pharmaceutically acceptable derivatives thereof.

According to our invention we also provide a pharmaceutical composition comprising (preferably less than 80%, and more preferably less than 50% by weight) of a compound of formula I, or a pharmaceutically acceptable salt, or where E is a —COOH group, ester or amide thereof, in combination with pharmaceutically acceptable adjuvant, diluent or carrier. Examples of suitable adjuvants, diluents or carriers are: for tablets, capsules and dragees; microcrystalline cellulose, calcium phosphate, diatomaceous earth, a sugar such as lactose, dextrose or mannitol, talc, stearic acid, starch, sodium bicarbonate and/or gelatin; for suppositories, natural or hardened oils or waxes; and for inhalation compositions, coarse lactose. The compound of formula I, or the pharmaceutically acceptable salt, or where E or $E_1$ is a —COOH group, ester or amide thereof, preferably is in a form having a mass median diameter of from 0.01 to 10 microns. The compositions may also contain suitable preserving, stabilising and wetting agents, solubilisers, sweetening and colouring agents and flavourings. The compositions may, if desired, be formulated in sustained release form. We prefer compositions which are designed to be inhaled.

The invention is illustrated, but in no way limited by the following Examples, in which temperatures are in degrees centigrade.

EXAMPLE 1

10-Propyl-2, 8-bis(1H-tetrazol-5-yl)-4H,6H-benzo[1,2-b:5,4-b']dipyran-4,6-dione (a) 4,6-Dioxo-10-propyl-4H,6H-benzo[1,2-b:5,4-b']dipyran-2,8-dicarboxamide Diethyl 4,6-dioxo-10-propyl-4H,6H-benzo[1,2-b:5,4-b']dipyran-2,8-dicarboxylate (2 g, 5 mmol) was dissolved in ethanol (100 ml) and ammonia gas passed through the solution for 2 hours. The flow of ammonia was then stopped and the reaction mixture stirred for a further hour. The resulting suspension was treated with ethanolic HC and water and then filtered to give the sub-title compound as a buff coloured solid on recrystalisation from methylene chloride (b) 4,6-Dioxo-10-propyl-4H,6H-benzo[1,2-b:5,4-b']dipyran-2,8-dicarbonitrile The product of step (a) (7.5 g, 21.9 mmol) was slowly added to a solution of $POCl_3$ (6.12 ml, 65.65 mmol) in dimethylformamide (500 ml) at 0°. The mixture was heated to 60° and held at that temperature for 42 hours. The reaction mixture was then cooled, poured into water, stirred for 1.5 hours, filtered, dried and recrystallised from acetone to give the sub-title compound as a dark pink solid.

(c) 4,6-Dioxo-10-propyl-4H,6H-benzo[1,2-b:5,4-b']dipyran-2[-di-(5H-tetrazole)

The product of step (b) (300 mg, 0.9 mmol), ammonium chloride (0.138 g, 2.5 mmol) and sodium azide (0.168 g, 2.58 mmol) were added slowly with stirring to dry dimethylformamide (50 ml). The temperature of the suspension was raised to 60° over 2 hours and kept at that temperature for a further 2.5 hours. The reaction mixture was then cooled and poured into water (150 ml) to form a clear solution. Dilute HCl was then added until the suspension was acidic. The resulting precipitate was filtered off, washed with water and chloroform, and dried to give the sub-title product.

(d) Disodium 10-propyl-2,8-bis(1H-tetrazol-5-yl)-4H,6H-benzo[1,2-b:5,4-b']dipyran-4,6-dione To the product of step (c) (3.5795 g, 8.9 mmol) in water (20 ml) was added with stirring 1.5132 g of sodium hydrodgen carbonate. The resulting solution was filtered, evaporated to half its volume, triturated with acetone (40 ml), left to stand, filtered and the precipitate washed with acetone. The solid was then dissolved in sterile water, filtered and freeze dried to give the disodium salt of the title compound.

Analysis Found: C: 36.80, H: 2.48, N: 19.80. 21.5% water Requires: C: 36,81, H: 2.29, N: 20.15.

EXAMPLE 2

4,6-Dioxo-10-propyl-8-(1H-tetrazol-5-yl)-4H,6H-benzo[1, 2-b;5,4-b']dipyran-2-carboxylate (a) Ethyl 8-aminocarbonyl-4,6-dioxo-10-propyl-4H,6H-benzo[1,2-b:5,4-b']dipyran-2-carboxylate Ethyl 4,6-dioxo-10-propyl-8-carboxy-4H,6H-benzo[1,2-b;5,4-b']dipyran-2-carboxylate (6.0 g, 16.13 mmol), thionyl chloride (1.50 ml, 20.5 mmoles) dry dimethylformamide (0.5 ml) and dry dichloroethane (100 ml) were stirred and heated under reflux for 1 hour.

The cooled reaction mixture was evaporated to dryness to afford a pale orange solid. This was suspended in dry dimethylformamide (50 ml) with stirring and cooled in an ice water bath. A solution of ammonia in dry dimethylformamide (1.8% w/v;.30.5 ml, 32.3 mmol) was added dropwise over 15 mins, followed by stirring at this temperature for 2 hours. The cooling bath was removed and stirring continued for 3 hours. Further ammonia in dimethylformamide (2 ml) was added at room temperature and stirring continued overnight.

The resulting suspension was diluted to 1200 ml with ethyl acetate and stirring continued for 1 hour. Water (200 ml) was then added and the near complete solutions separated. The aqueous phase which had been made basic with $NaHCO_3$ was extracted with further ethyl acetate, and the combined organic layers were washed with sat. brine, filtered and separated. The organic phase was dried quickly with $Na_2SO_4$, washing the desiccant well with ethyl acetate, and evaporated to afford a semi-solid residue. Trituration with ether (200 ml) and filtration afforded the sub-title product (5.24 g) off white plates from ethanol, mp 229°–231°.

| | Analysis | | |
|---|---|---|---|
| | C | H | N |
| $C_{19}H_{17}NO_7$ requires | 61.45 | 4.62 | 3.77 |
| found | 61.73 | 4.77 | 3.75 |

(b) Ethyl 8-cyano-4,6-dioxo-10-propyl-4H,6H-benzo-[1,2-b:5,4-b']dipyran-2-carboxylate Phosphoryl chloride (1.50 ml, 16.18 mmole) was added dropwise to stirred dimethylformamide (65 ml) with ice-cooling over 10 mins. The product of step (a) (4.0 g, 10.75 mmol) was added in one portion and the suspension heated at 50–55° for 30 mins. The cooled reaction mixture was poured into vigorously stirred brine (3 l) and the precipitated solid collected by filtration, dissolved in ethyl acetate (400 ml) washed with sat. brine, dried ($MgSO_4$) and evaporated to afford a fawn-coloured solid 3.77 g, which was recrystallised from 60°–80 ° petroleum ether (75 ml) evaporating to 110 ml to afford the sub-title product as cream coloured plates, 2.52 g after vacuum-drying at 70 °. mp 182°–4°.

| Analysis | | | |
|---|---|---|---|
| | C | H | N |
| $C_{19}H_{15}NO_6$ requires | 64.59 | 4.28 | 3.96 |
| found | 64.49 | 4.01 | 4.40 |

(c) Ethyl 4,6-dioxo 10-propyl-8-(1H-tetrazol-5-yl)-4H, 6H-benzo[1,2-b;5,4-b']dipyran-2-carboxylate A mixture of the product of step (b) (2.34 g, 6.63 mmole), ammonium chloride (0.44 g, 8.22 mmol), sodium azide (0.53 g, 8.15 mmole) and dry dimethylformamide (45 ml) was heated on a steam bath for 2.75 hours then allowed to cool overnight, and poured with vigorous stirring into sat. brine (1.5 l) and dil.HCl (1 l). The precipitated solid was collected by filtration, washed well with water, then ether and vacuum-dried over $P_2O_5$. The product was Soxhlet extracted with acetone, evaporating to a final volume of 140 ml. On cooling the product separated as a tan coloured solid, 1.53 g, after vacuum drying at 70°.

| Analysis | | | |
|---|---|---|---|
| | C | H | N |
| $C_{19}H_{16}N_4O_6$ requires | 57.57 | 4.07 | 14.14 |
| found | 57.18 | 4.08 | 13.97 |

(d) Disodium 4,6-dioxo-10-propyl-8-(1H-tetrazol-5-yl)-4H,6H-benzo[1,2-b;5,4-b']dipyran-2-carboxylate Sodium hydroxide (12.62 ml of 0.1 M solution) was added over 30 mins to a stirred suspension of the product of step (c) (0.25 g) in methanol (25 ml) whilst heating under reflux.

The reaction mixture was then filtered and evaporated to form a yellow semi-solid residue. This solid was dissolved in methanol, filtered and the product precipitated with ether. The resulting yellow solid was dissolved in sterile water, filtered and freeze-dried to afford the sub-title product as a yellow solid 1.288 g.

| Analysis | | | | |
|---|---|---|---|---|
| | C | H | N | $H_2O$ |
| Found | 44.07 | 3.40 | 12.02 | 10.3 |
| $C_{17}H_{10}N_4Na_2O_6$ requires for 10.3% $H_2O$ | 44.42 | 3.32 | 12.18 | |

EXAMPLE 3

8-Aminocarbonyl-4,6-dioxo-10-propyl-4H,6H-benzo[1,2-b: 5,4-b']dipyran-8-carboxylic acid (a) 8-Aminocarbonyl-4,6-dioxo-10-propyl-4H,6H-benzo[1,2-b: 5,4-b']dipyran-2-carboxylic acid Sodium hydroxide solution (0.1 M 41.3 ml) was added with stirring to a refluxing suspension of the amide from Example 1(a) (1.53 g) in methanol (125 ml). When the addition was complete the resulting solution was cooled, added to water (1L) and hydrochloric acid (dil, 50 ml) added to give a precipitate. Recrystallisation from acetone:water gave the title compound as off white needles (0.895 g), mp 322°-32 4° (decomp.).

(cb) Sodium 8-aminocarbonyl-4,6-dioxo-10-propyl-4H,6H-benzo[1,2-b: 5,4-b']dipyran-2-carboxylate The acid amide from step (b) (0.85 g) and sodium bicarbonate (0.206 g) were stirred in water (50 ml) at room temperature until a clear, yellow solution was attained. Filtration, followed by freeze drying gave the sodium salt of the title compound as a pale yellow solid.

$C_{17}H_{12}NNaO_7, 5\% H_2O$ Requires: C: 52.72, H: 3.23, N: 3.65. Found: C: 53.10, H: 3.64, N:3.63%.

EXAMPLE 4

8-(N,N-Dimethylcarbonylamino)-4,6-dioxo-10-propyl-4H, 6H-benzo[1,2-b:5,4-b']dipyran-2-carboxylate (a) Ethyl 8-[N,N-dimethylcarbonylamino]-4,6-dioxo-10-propyl-4H,6H-benzo[1,2-b:5,4-b]dipyran-2-carboxylate To a stirred solution of 33% w/v dimethylamine in methanol (25 ml) in dry ether, (100 ml), was added, over 5 minutes, portions of finely powdered 4-nitrophenyl 4,6-dioxo-10-propyl-4H,6H-benzo[1,2-b:5,4-b']dipyran-2,8-dicarboxylate, (15 g). The mixture was kept under reflux for 30 minutes then volatiles were removed.

The residue was dissolved in ethanol, (40 ml) treated with conc. hydrochloric acid (1 ml) and heated under reflux for 10 minutes then evaporated. The residue was extracted into chloroform and then washed with water, dried ($MgSO_4$), filtered and evaporated. Recovered material was dissolved in hot ethyl acetate and crystallised from an ethyl acetate/60°-80° petrol mixture to give, sub-title material, (3.7 g) m.p. 270° (d).

(b) 8-(N,N-Dimethylcarbonylamino)-4,6-dioxo-10-propyl-4H,6H-benzo[1,2-b:5,4-b']dipyran-2-carboxylic acid The product of Step (a) (3.6 g) and sodium bicarbonate, (1.2 g) were treated with aqueous methanol and heated under reflux for 30 minutes to give a clear solution. The alcohol was evaporated off and the concentrate was diluted with water, filtered then acidified with dilute hydrochloric acid. A precipitate was obtained and was filtered off, washed with water and dried to give the sub-title compound as a cream powder, (2.2 g), m.p. 267°-2 70°(d).

(c) Sodium 8-(N,N-dimethylcarboxamido)-4,6-dioxo-10-propyl-4H,6H-benzo[1,2-b:5,4-b']dipyran-2-carboxylate The product of Step (b) (2.2 g) and sodium bicarbonate, (0.5 g) were mixed and dissolved in water, (6 ml). The resulting solution was filtered and then added dropwise to anhydrous acetone. A precipitate was obtained which was filtered off and crystallised from a methanol/acetone/ water mixture and dried in vacuo to give the sodium salt of the title compound as a grey powder (1.3 g).

Analysis Found C,51.54(H,3.92);N,3.05,$H_2O$,9.63% (unencapsulated), $C_{19}H_{16}N$ $NaO_7, 3H_2O$ requires C,51.00,(H,4.92);N,3.13;$H_2O$,12%.

EXAMPLE 5

8-(4-Carboxyphenyl)-4,6-dioxo-10-propyl-4H, 6H-benzo [1,2-b:5,4-b']dipyran-2-carboxylic acid (a) Ethyl 6-acetyl-7-(4-methoxycarbonylbenzoyloxy)-4-oxo-8-propyl-4H-1-benzopyran-2-carboxylate Ethyl 6-acetyl-7-hydroxy-4-oxo-8-propyl-4H-[3,2-b]benzopyran-2-carboxylate (1.5 g, 4.7 mmol) and p-methoxycarbonylbenzoyl chloride (975 mg, 4.9 mmol) in dry pyridine (20 ml) were heated on a steam bath for 4 hours. The mixture was then poured into concentrated hydrochloric acid and extracted with ethyl acetate (3 times). The organic layers were washed with 2M hydrochloric acid, water, dilute sodium bicarbonate solution (3 times) and water (twice), dilute sodium bicarbonate solution (3 times) and water (twice), and then dried to yield on removal of solvent a pale yellow solid. Recrystallisation from ethanol gave the sub-title compound as off white crystals, 1.86 g. $^1$H NMR (CDCl$_3$), δ:8.61 (s,1H); 8.27 (ABq, 4H); 7.9 (s,1H); 4.60 (q,2H); 4.00 (s,3H); 3.00 (t,2H); 2.64 (s,3H); 1.7 (m,2H); 1.51 (t,3H); 1.02 (t,3H).

(b) 8-(4-Carboxyphenyl)-4,6-dioxo-10-propyl-4H,6H-benzo [1,2-b:5,4-b']dipyran-2-carboxylic acid, mixed dimethyl and methyl ethyl esters The product of step (a) (2 g, 4M mmol) and sodium hydride (50% oil suspension, 1.4 g, 29 mmole) were stirred under nitrogen at room temperature in 1,4-dioxan for 0.5 hours, then heated under reflux for a further 5 hours.

The product mixture was poured into methanolic hydrochloric acid (200 ml) and heated under reflux for 1 hour. The yellow solution was then poured into water and extracted with ethyl acetate (3 times). The combined organics were washed with water (twice), dried (anhydrous sodium sulphate) and evaporated to give a grey solid which was refluxed with methanol (500 ml) for 15 minutes. The suspension was allowed to cool to room temperature and grey solid filtered off and dried over phosphorus pentoxide to yield 930 mg of a 5:2 mixture of the sub-title dimethyl and methyl ethyl esters. Concentration of the mother liquors gave a further 320 mg of the desired product.

(c) (4-Carboxyphenyl)-4,6-dioxo-10-propyl-4H,6H-benzo [1,2-b:5,4-b']dipyran-2-carboxylic acid The diester of step (b) (175 mg, 0.39 mmol) was heated under reflux in acetic acid (20 ml) and concentrated hydrochloric acid (5 ml). After 8 hours further concentrated hydrochloric acid (3 ml) was added and reflux continued overnight. The mixture was allowed to cool and stand at room temperature for 24 hours, then the greyish solid filtered off and washed to give the title product, 155 mg, mp 250°. $^1$H NMR (d$^6$ (CD$_3$)$_2$SO);δ:8.55 (s,1H); 8.20 (ABq, 4H); 7.21 (s,1H); 6.96 (s,1H); 3.22 (m,2H); 1.8 (m,2H); 1.03 (t,3H).

Elemental analysis: C$_{23}$H$_{16}$O$_8$ Requires: C:65.71, H:3.84%; Found: C:65.56, H:3.81%.

(d) Disodium 8-(4-Carboxyphenyl)-4,6-dioxo-10-propyl)-4H,6H-benzo[1,2-b:5,4-b']dipyran-2-carboxylate The diacid from step (c) (920 mg, 2.19 mmol) was treated with sodium bicarbonate (368 mg; 4.38 mmol) in water (25 ml). Addition of acetone precipitated a pale red brown solid which was filtered off, dissolved in water, filtered through a millipore filter (0.45 micron) and freeze dried to give the disodium salt of the title compound, 997 mg.

Elemental analysis: C$_{23}$H$_{14}$Na$_2$O$_8$. 4H$_2$O Requires: C:51.49; H:4.13; Na:8.57%; Found: C:51.38; H:2.59; Na:8.55.

EXAMPLE 6

3-(8-Carboxy-4,6-dioxo-10-propyl-4H,6H-benzo[1,2-b:5,4-b']-dipyran-2-)propanoic acid (a) Ethyl 6-acetyl-7-hydroxy-4-oxo-8-propyl-4H-1-benzopyran-2-carboxylate 4,6-Dioxo-10-propyl-4H,6H-benzo[1,2-b:5,4-b']dipyran-2,8-dicarboxylic acid (3.44 g) and sodium bicarbonate (3.4 g) were heated together in ethanol (25 ml) and water (25 ml) under reflux with mechanical stirring for five hours. Water (300 ml) was added and the mixture was washed with ether. The mixture was acidified and extracted with ether. The ether extracts were combined washed with water and brine then dried and evaporated to leave a pale yellow solid (2.3 g). The solid was dissolved in dry ethanol (100 ml) and heated under reflux for two hours during which time hydrogen chloride gas was passed through the solution. The cooled solution was concentrated in vacuo and the resultant solid crystallised from ethanol to afford prisms 1.54 g. Recrystalisation from ethyl acetate/ether gave the sub-title compound 1.06 g mp 129°-131°.

NMR CDCl$_3$,δ,12.9(s,1H) 8.55(s,1H) 7.0(s,1H) 2.75(s,3H).

(b) Ethyl (6-Acetyl-2-ethoxycarbonyl-4-oxo-8-propyl(-4H-1-benzo-pyran-7-yl)succinate Ethyl 6-acetyl-7-hydroxy-4-oxo-8-propyl-4H-1-benzopyran-2-carboxylate (5 g) in dry dimethylformamide (100 ml) was added dropwise to an ether washed suspension of sodium hydride (0.8 g of 50% in oil) stirred in dry dimethylformamide (200 ml) under nitrogen. After addition was complete the mixture was stirred for a further thirty minutes. A solution of ethyl succinyl chloride (2.37 ml) in dry dimethylformamide (50 ml) was added dropwise to the red solution and the mixture then heated at 60° for two hours. The mixture was poured onto water (500 ml) containing concentrated hydrochloric acid (50 ml) and ether extracted. The combined extracts were washed with dil. hydrochloric acid, water, saturated sodium bicarbonate solution and water then dried and evaporated. Crystallisation from cyclohexane gave the sub-title compound as colourless prisms 4.9 g mp 76°-78°.

NMR (CDCl$_3$),δ, 8.52(s,1H) 7.12(s,1H) 2.63(s,3H) 1.45(t,3H) 1.30(t,3H) 1.0(t,3H) 4.48(q,2H) 4.20(q,2H) 2.9(m,2H) 1.7(m,2H).

(c) Ethyl 3-(8-ethoxycarbonyl-4,6-dioxo-10-propyl-4H,6H-benzo[1,2-b:5,4-b']dipyran-2-)propanoate A solution of ethyl (6-acetyl-2-ethyoxycarbonyl-4-oxo-8-propyl-4H-1-benzopyran-7-yl) succinate (10.9 g) in dry dioxan (200 ml) was added dropwise to a stirred suspension of ether washed sodium hydride (2.75 g of 50% in oil) in dry dioxan (500 ml) under a nitrogen atmosphere. After addition was complete ethanol (one drop) was added and the mixture heated to 80° and stirred at this temperature for four hours. After cooling the mixture was diluted with water (500 ml) acidified with dilute hydrochloric acid and extracted with chloroform. The combined extracts were washed with dilute hydrochloric acid and water then dried and evaporated to leave an oil. The oil was dissolved in ethanol (300 ml) conc. hydrochloric acid (5 ml) added and the mixture heated under reflux for three hours. The mixture was concentrated in vacuo and the residue crystallised from ethanol to afford the sub-title compound as buff prisms 3.4 g mp 131°–133°.

CHN: Theory: C, 64.48; H, 5.65. Found: 64.34; 5.84.

(d) Disodium 3-(8-carboxy-4,6-dioxo-10-propyl-4H,6H-benzo-[1,2-b:5,4-b']dipyran-2-)propanoate Ethyl-8-ethoxycarbonyl-4,6-dioxo-10-propyl-4H, 6H-benzo[1,2-b:5,4-6']dipyran-2-propanoate (1g) was heated in methanol (200 ml) under reflux. Sodium hydroxide solution (43.5 ml of 0.1016 M) was added dropwise over two hours. The mixture was heated for a further two hours then the mixture concentrated in vacuo to 2 ml. Acetone (500 ml) was added and the precipitate collected. The solid was dissolved in water and dilute hydrochloric acid added. After ten minutes the product was collected. Purification by reverse phase HPLC gave 340 mg of the title compound.

CHN: Found: C, 57.18; H, 4.99. Req. for 61.7%$H_2O$: 57.18 4.78.

The diacid (340 mg) was stirred in distilled water (40 ml) with sodium bicarbonate (144 mg). When complete solution was attained the solution was freeze dried to leave the disodium salt of the title compound, as a fine white solid 348 mg. NMR ((CD$_3$)$_2$SO, δ) 8.44(s,1H) 6.68(s,1H) 6.20(s,1H) 3.09(t,2H) 2.88(t,2H) 2.35(t,2H) 1.70(m,2H) 0.91(t,3H).

CHN: Found: C:42.93, H:4.92. Req. for 21.7% $H_2O$: C:42.93, H:5.06.

EXAMPLE 7

4,6-Dioxo-12-propyl-4H,6H-[1]-benzopyrano[3,2-g][1]benzopyran-2,8-dicarboxylic acid

(a) 4-[4-Acetyl-3-hydroxy-2-propylphenoxy]isophthalic acid

A solution of dimethyl 4-bromoisophthalate (2.73 g) and 2,4-dihydroxy-3-propylphenylethanone (1.94 g) in nitrobenzene (20 ml) was heated at 140° under nitrogen for 3 hours with copper powder (200 mg) and potassium carbonate (2.7 g). The solution was cooled and a solution of sodium hydroxide (1.6 g) in water (8 ml) and ethanol (22 ml) ws added. The mixture was heated under reflux for one hour. The cooled mixture was poured onto ice-water and washed with dichloromethane. The aqueous solution was acidified with hydrochloric acid and the precipitate collected. Crystallisation from 20% aqueous ethanol gave the sub-title compound as a brown solid 0.8 g mp 280°–283°.

(b) 7-Acetyl-6-hydroxy-5-propylxanthane-2-carboxylic acid

4-[4-Acetyl-3-hydroxy-2-propylphenoxy]isophthalic acid (0.8 g) was dissolved in sulpholane (10 ml) and heated to 80°. Polyphosphoric acid (10 ml) was added and the solution stirred for 4 hours. The mixture was poured onto water and the precipitate collected to afford the sub-title compound as a pale brown solid 0.65 g, mp >300°.

(c) Ethyl 7-acetyl-6-hydroxy-5-propylxanthane-2-carboxylate

7-Acetyl-6-hydroxy-5-propylxanthane-2-carboxylic acid (3.4 g) was dissolved in ethanolic hydrogen chloride (250 ml) and the solution heated under reflux for 3 hrs. The mixture was concentrated in vacuo and the residue taken up in water, neutralised with sodium carbonate solution and extracted with chloroform. The solution was dried and evaporated to leave the sub-title compound as a brown solid which was crystallised from ethanol as pale brown plates 1.7 g mp 200°–201°.

(d) Diethyl 4,6-dioxo-12-propyl-4H-6H[1]benzopyrano[3,2-g][1]benzopyran-2,8-dicarboxylate A solution of ethyl 7-acetyl-6-hydroxy-5-propylxanthane-2-carboxylate (3.68 g) in ethanol (20 ml) was added to a solution of sodium ethoxide prepared from ethanol (80 ml) and sodium (2 g). After stirring for 5 mins diethyl oxalate (4 ml) was added. The mixture was stirred for 1 hr to produce a bright yellow suspension. The mixture was poured onto ice-water and acidified with hydrochloric acid and extracted with ethyl acetate. The ethyl acetate was dried and concentrated in vacuo. The residue was taken up in ethanolic hydrogen chloride and left at room temperature for 16 hrs. The mixture was diluted with water and extracted with dichloromethane. The dichloromethane was washed with sodium bicarbonate solution and brine then dried and evaporated to give a pale brown solid 3.5 g mp 195°–210°. Crystallisation from toluene (twice) gave the sub-title compound as colourless plates 1.1 g mp 218°–220°.

(e) 4,6-Dioxo-12-propyl-4H-6H-[1]benzopyrano[3,2-g][1]benzopyran-2-8-dicarboxylic acid Diethyl 4,6-dioxo-12-propyl-4H-6H-[1]benzopyrano[3,2-g][1]benzopyran-2-8-dicarboxylate[2.75 g] was stirred in conc. sulphuric acid (90 ml) and the mixture heated keeping the temperature between 70° and 80° for three hours. The cooled mixture was poured onto ice-water and the precipitate collected and washed with water. Crystallisation from dimethylformamide produced the sub-title compound as pale yellow prisms 1.9 g mp >300°.

(f) Disodium 4,6-dioxo-12-propyl-4H,6H-[1]-benzopyrano[3,2-g][1]benzopyran-2,8-dicarboxylate 4,6-Dioxo-12-propyl-4H-6H-[1]benzopyrano[3,2-g][1] benzopyran 2,8-dicarboxylic acid (1.9 g) was suspended in water (50 ml) and sodium bicarbonate (770 mg) added portionwise over 30 mins. The mixture was stirred for a further ten minutes then filtered. Acetone was added to precipitate the product which was collected and washed with acetone. The solid was dissolved in water, filtered and the solution freeze dried to leave the disodium salt of the title compound as a white powder 860 mg.

Analysis

Found: C,47.77; H,2.39. Req for 16.3% $H_2O$: 48.17; 2.31–4.10.

$H_2O$ 16.3% weight loss by thermogravimetric analysis (TGA) at 200°.

EXAMPLE 8

6,7,8,9-Tetrahydro-4-oxo-10-propyl-4H-naphtho[2,3-b]pyran-2,7-dicarboxylic acid

(a) Ethyl 6-methoxy-1-oxo-1,2,3,4-tetrahydronaphthalene-2-carboxylate

A solution of 6-methoxy-1-oxo-1,2,3,4-tetrahydronaphthalene (3 g) in tetrahydrofuran (30 ml) was added slowly to a solution of diethyl carbonate (5.85 ml) in tetrahydrofuran (150 ml) containing a suspension of sodium hydride (50% in oil, 3.28 g) over a period of 30 minutes. The mixture was treated at reflux with stirring, for 4 hours. Acetic acid (6 ml) then dilute HCl (20 ml) were added dropwise, and the bulk of the tetrahydrofuran removed by evaporation. The residue was taken up in ether (100 ml), washed with saturated brine and evaporated to give the sub-title compound as an orange oil (4.4 g).

(b) Ethyl 6-methoxy-1,2,3,4-tetrahydronaphthalene-2-carboxylate

The ketoester from step (a) (2.6 g) was mixed with palladium on charcoal catalyst (10%, 0.25 g) suspended in acetic acid (10 ml) and added to acetic acid (10 ml) containing 10 drops of perchloric acid. The mixture was then hydrogenated at 3 atmospheres pressure at room temperature for 18 hours. The mixture was filtered to remove catalyst, evaporated to a residue, the residue dissolved in ethyl acetate, washed, separated and dried to give on evaporation the sub-title compound as an orange oil, bp 130°–40°,/0.03 mm.

(c) Ethyl 7-acetyl-6-hydroxy-1,2,3,4-tetrahydronaphthalene-2-carboxylate

The methoxy ester from step (b) (1.73 g) was heated under reflux with hydrobromic acid (48% aqueous solution, 8 ml) for 2 hours and then evaporated to dryness, to give an orange oil. This oil was dissolved in boron trifluoride:acetic acid complex (15 ml) and heated on a steam bath. After 1.25 hours the reaction mixture was poured into saturated brine (400 ml), the pH adjusted to about 5 by the addition of saturated aqueous sodium bicarbonate and the mixture stirred overnight. Ethyl acetate was added, the organic layer separated, washed with saturated brine, dried and evaporated to give the sub-title compound (1.89 g), colourless solid from pentane, mp 73°–5°.

(d) Ethyl 7-acetyl-6-prop-2-enyloxy-1,2,3,4-tetrahydronaphthalene-2-carboxylate The product from step (c) (42.6 g), 3-bromopropene (17.5 ml) and potassium carbonate (27 g) were heated at 55° with stirring in dimethylformamide (250 ml) containing a one crystal of potassium iodide. After 24 hours, the reaction mixture was cooled, poured into iced brine (4 l) and the pale yellow precipitate formed collected by filtration. The precipate was washed, dried and recrystallised from petrol (bp 30°–40°) to give the sub-title compound as pale yellow crystals, 27.0 g.

(e) 7-acetyl-6-hydroxy-5-prop-2-enyl-1,2,3,4-tetrahydronaphthalene-2-carboxylate The product from step (d) (0.5 g) was heated under reflux under an atmosphere of nitrogen in N-methylpyrolidone (4 ml) for 1.5 hours. The reaction mixture was then poured into saturated brine (250 ml), to give a precipitate which on filtration, washing and drying gave the sub-title compound as an orange powder, 0.49 g.

(f) Ethyl-7-acetyl-6-hydroxy-5-propyl-1,2,3,4-tetrahydronaphthalene-2-carboxylate The product of step (e) (0.49 g) was hydrogenated at atmospheric pressure at room temperature in ethanol (100 ml) with palladium on charcoal (5%, 50 mg) as catalyst. Filtration to remove catalyst, followed by evaporation of the filtrate gave the sub-title compound as a colourless solid, 0.43 g.

(g) Diethyl 6,7,8,9-tetrahydro-4-oxo-10-propyl-4H-naphtho[2,3-b]pyran-2,7-dicarboxylate The product of step (f) (0.42 g) was added to a stirred solution of diethyl oxalate (0.56 ml) and sodium ethoxide (from 0.16 g sodium) in ethanol (25 ml). The mixture was heated at reflux for 40 minutes then cooled to room temperature then ethanolic HCl added (15 ml). The mixture was then heated for an hour, the solvent removed by evaporation and the residue separated between ethyl acetate and water. The organic layer on washing, drying and evaporation gave the sub-title compound as an oil which crystallised on standing, (0.58 g), mp 89.5°–90.5°.

(h) 6,7,8,9-Tetrahydro-4-oxo-10-propyl-4H-naphtho[2,3-b]pyran-2,7-dicarboxylic acid The product of step (g) (2.3 g), glacial acetic acid (30 ml) and concentrated hydrochloric acid (15 ml) were heated at reflux for 1 hour, then cooled and filtered to give the title compound, as a white powder (1.88 g) mp 271°–2°.

(i) Disodium 6,7,8,9-tetrahydro-4-oxo-10-propyl-4H-naphtho[2,3-b]pyran-2,7-dicarboxylate The product of step (h) (1.758 g) and sodium bicarbonate (0.885 g) were stirred in water (5 ml) at room temperature until complete dissolution occurred. The solution was filtered and then poured into acetone (400 ml) with vigarous stirring. The precipitate that formed was dissolved in water (20 ml) and freeze dried, to give the disodium salt of the title compound as a colourless solid, (1.654 g).
$C_{18}H_{16}Na_2O_6, 5H_2O$ requires C:46.13 H:4.24 Na:10.9%. found C:46.56 H:5.64 Na:9.91%.

EXAMPLE 9

6,7,8,9-Tetrahydro-5-hydroxy-4-oxo-10-propyl-4H-naphtho[2,3-b]pyran-2,7-dicarboxylic acid

(a) Diethyl 6,7,8,9-Tetrahydro-5-nitro-4-oxo-10-propyl-4H-naphtho[2,3-b]pyran-2,7-dicarboxylate The diester from Example 10(g) (1g) was dissolved in concentrated sulphuric acid (5 ml) with stirring and cooled to 0°. Fuming nitric acid (0.3 ml) was added dropwise over 10 minutes, the ice bath was then removed and the reaction mixture was stirred at room temperature for 30 minutes. The mixture was then poured into the water, vigorously stirred and the resulting precipitate collected by filtration. Recrystallisation from petrol (bp 60°–80°)/acetone gave the sub-title compound as colourless needles. (0.9 g), mp 164°–6°.

(b) Diethyl 5-amino-6,7,8,9-tetrahydro-4-oxo-10-propyl-4H-naphtho[2,3-b]pyran-2,7-dicarboxylate The diester from step (a) (7.62 g) was dissolved in hot ethyl acetate (500 ml). The resulting solution was cooled to room temperature and hydrogenated at atmospheric pressure in the presence of palladium on charcoal (5 %, 0.75 g). After 90 hours, the reaction mixture was filtered to remove catalyst and the filtrate evaporated to give the sub-title product as orange needles (4.81 g), from petrol (bp 60°–80°/acetone), mp 102°–103°.

(c) Diethyl 6,7,8,9-tetrahydro-5-hydroxy-4-oxo-10-propyl-4H-naphtho[2,3-b]pyran-2,7-dicarboxylate The amine from step (b) (4.65 g) was dissolved in sulphuric acid (50%), (60 ml) at room temperature and then cooled to 0°.

A solution of sodium nitrite (1.20 g) in water (8 ml) was added dropwise over 30 minutes, whilst maintaining the internal temperature between 2°–4°. The cooled reaction mixture was then added in 1 ml portions to sulphuric acid solution (20%, 190 ml) containing urea (9.3 g) maintained at a temperature of 140°. The sulphuric acid soution was maintained at this temperature for a further 2 hours after the addition was complete, then cooled and poured into water (2l). The resulting precipitate was filtered off and esterified with ethanolic HCL, evaporated to dryness to give the sub-title compound as yellow needles (3.40 g), from ethanol, mp 107°–9°.

(d) 6,7,8,9-Tetrahydro-5-hydroxy-4-oxo-10-propyl-4H-naphtho[2,3-b]pyran-2,7-dicarboxylic acid The product of step (c) (1.20 g), glacial acetic acid (15 ml) and concentrated hydrochloric acid (9 ml) were heated with stirring at reflux for 4.5 hours. The mixture was cooled and the title product collected by filtration as a yellow solid (1.00 g) mass spec. m/e 346.

(e) Disodium 6,7,8,9-Tetrahydro-5-hydroxy-4-oxo-10-propyl-4H-naphtho[2,3-b]pyran-2,7-dicarboxylate A solution of sodium bicarbonate (0.51 g) in water (10 ml) was added to a stirred suspension of the diester from step (d) (1.065 g) in water (5 ml) to give a clear solution. The solution was evaporated to dryness and the residue dissolved in methanol (50 ml). The methanol solution was poured into ether to give a pale yellow solid, which was dissolved in water and freeze dried to give the disodium salt of the title product (1.09 g).

$C_{18}H_{16}Na_2O_7$, 11.79%$H_2O$ requires C48.86 H4.58 $H_2O$ 11.79%. found C48.86 H4.94 $H_2O$ 11.79%.

EXAMPLE 10

6,7,8,9-Tetrahydro-5-hydroxy-4-oxo-10-propyl-4H-naphtho[2,3-b]pyran-2,8-dicarboxylic acid The title acid was prepared from the corresponding diethyl ester, mp 306°–308° (dec.).

The disodium salt of the title acid was prepared by the method Example 9(e), uv spectrum: λmax. (ε) 206, (22750); 256, (13500); 270; 360.

EXAMPLE 11

7,8,9,10-Tetrahydro-1-oxo-5-propyl-1H-naphtho[2,1-b]pyran-3,8-dicarboxylic acid (a) Diethyl 7,8,9,10-tetrahydro-1-oxo-15-propylnaphtho[2,1-b]pyran-3,8-dicarboxylate Ethyl 5-acetyl-6-hydroxy-7-propyl-1,2,3,4-tetrahydro naphthalene-2-carboxylate (1.6 g) (isolated as a by product from a large scale preparation of Example 8 (f) was reacted with diethyl oxalate (4 ml) and sodium ethoxide in ethanol by the method of Example 8(g). Work up gave the sub-title product as off white needles (1.48 g), mp 107.5°–109°.

(b) 7,8,9,10-Tetrahydro-1-oxo-5-propyl-1H-naphtho[2,1-b]pyran-3,8-dicarboxylic acid The diester from step (a) (1.16 g) glacial acetic acid (15 ml) and concentrated hydrochloric acid (10ml) were heated at reflux for 3 hours, allowed to cool and the resulting precipitate collected by filtration, to give the title compound as a colourless solid, (1.067 g), mp 305–306 (dec).

(c) Disodium 7,8,9,10-Tetrahydro-1-oxo-5-propyl-1H-naphtho[2,1-b]pyran-3,8-dicarboxylate The diacid (1.002 g) from step (b) and sodium bicarbonate (0.505 g) were stirred in water (10 ml) at room temperature until a clear solution was obtained. Filtration the solution followed by freeze drying gave the disodium salt of the title compound, as a colourless solid (1.036 g).

u.v. spectrum: λmax (ε) 207, (17529); 243, (17711); 323, (5660).

EXAMPLE 12

6-Methoxyimino-4-oxo-10-propyl-4H,6H-benzo[1,2-b:5,4-b']dipyran-2,8-dicarboxylic acid (a) Diethyl 6-methoxyimino-4-oxo-10-propyl-4H,6H-benzo[1,2-b:5,4-b']dipyran-2,8-dicarboxylate A mixture of diethyl 4,6-dioxo-10-propyl-4H,6H-benzo[1,2-b:5,4-b']dipyran-2,8-dicarboxylate (2.0 g, 5.0 mmole) and methoxyamine hydrochloride (0.42 g, 5 mmole) in dry ethanol (40 ml) was heated under reflux with stirring during 2 hours. After cooling to room temperature, a yellow crystalline solid was collected by filtration and air-dried. Recrystallisation from ethanol, followed by column chromatography on silica (100 g), eluting with a mixture of 3:1 petroleum ether-ether, and finally recrystallisation from 60°–80° petroleum ether afforded the sub-title compound as a pale yellow crystalline solid (0.22 g, 21%), mp 175°–9°.

$C_{22}H_{23}NO_8$ requires C:61.53%, H:5.40%, N:3.26%. Found C:61.44%, H:5.39%, N:3.40%.

(b) Disodium 6-methoxyimino-4-oxo-10-propyl-4H,6H-benzo[1,2-b:5,4-b']dipyran-2,8-dicarboxylate An aqueous solution of sodium hydroxide (10.1 ml, 1.0M) was added dropwise over 3.75 hours to a stirred solution of the product of step a) (2.20 g, 5.12 mmole) in pure methanol (150 ml), maintained at reflux temperature. The resulting solution was filtered and evaporated to afford a semi-solid residue, which was taken into a minimum of water (9 ml) and added to stirred pure acetone (1500 ml). The product was collected by filtration and dried in vacuo at 60° to afford the required disodium salt as a pale yellow solid (2.08 g, 85%)

$C_{18}H_{13}NNa_2O_8$.3.5 $H_2O$ Requires: C:45.00%, H:2.91%, N:13.12%. Found: C:44.71%, H:2.95%, N:13.51%.

EXAMPLE 13

5-Oxo-9-propyl-5H-furo[3,2-g][1]-benzopyran-2,7-dicarboxylic acid (a)

1-[2-Hydroxy-4-(2-propenyloxy)-3-propylphenyl]ethanone 1-(2,4-Dihydroxy-3-propylphenyl)ethanone (19.4 g), allyl bromide (10.5 g), and anhydrous potassium carbonate (15.2 g) were stirred in dry acetone (200 ml) under reflux for 17 hours. The reaction mixture was cooled, poured into water and the precipitated product extracted with ether, which was washed with water and dried. The solvent was evaporated to leave an orange solid which was recrystallised from 30°-40° petroleum ether to give the sub-title product as 19.9 g of orange needles, m.p. 47°-49°.

Analysis: Found: C; 71.85% H; 7.7%. $C_{14}H_{18}O_3$ Requires: C; 71.8% H; 7.69%.

(b)

1-[2,4-Dihydroxy-5-(2-propenyl)-3-propylphenyl]ethanone

The product of step (a) (16.6 g) in N,N-diethylbenzeneamine (120 ml) was heated at reflux for 5 hours. The solvent was evaporated under reduced pressure and the residue, which solidified on cooling, was recrystallised from 60°-80° petroleum ether to give 14.3 g of the sub-title product as fluffy needles, mp 87°-88° C.

Analysis: Found: C; 71.84% H; 7.78%. $C_{14}H_{18}O_3$ Requires: C; 71.8% H; 7.69%.

(c) E & Z-1-[2,4-Dihydroxy-5-(1-propenyl)-3-propyl)phenyl ethanone

The product of step (b) (12 g) and potassium t-butoxide (18.7 g) were stirred at room temperature in dry dimethylsulphoxide (200 ml) under nitrogen for 17 hours at room temperature and then 30°-35° in an oil bath for 40 hours. The reaction mixture was poured into water, acidified and extracted with ether. The ethereal extract was washed well with water and dried. The solvent was evaporated to leave 12 g of residue, which was shown to be a mixture of the desired E & Z isomers by nmr spectroscopy.

The two isomers were separated by high pressure liquid chromatography to give the E isomer, mp 114°-116°.

Analysis: Found: C; 71.95% H; 7.9%. $C_{14}H_{18}O_3$ Requires: C; 71.8% H; 7.69%.

The Z isomer had mp 58°-60°.

Analysis: Found: C; 71.5% H; 7.71%. $C_{14}H_{18}O_3$ Requires: C; 71.8% H; 7.69%.

(d) Ethyl 7-hydroxy-4-oxo-6-(1-propenyl)-8-propyl-4H-1)benzopyran-2-carboxylate (mixture of E & Z isomers)

The mixture of E and Z isomers from step (c) above (1.17 g) and diethyl oxalate (1.7 ml) were dissolved in dry dimethylformamide (20 ml) and added to ether washed 50% sodium hydride (0.96%) suspended in dry dimethylformamide (20 ml) with stirring under nitrogen. The reaction mixture was stirred for 4 hours at room temperature, poured into dilute hydrochloric acid and extracted with ethyl acetate, which was then washed with water and dried. The solvent was evaporated, the residue treated with ethanol previously saturated with hydrogen chloride gas, and left to stand for 10 min. The reaction mixture was poured into water and the precipitated product collected by filtration, and dried to give 1.38 g of product, mp 182°-185°.

Analysis: Found: C; 67.9% H; 6.47%. $C_{18}H_{20}O_5$ Requires: C; 68.4% H; 6.33%.

(e) Ethyl 6-formyl-7-hydroxy-4-oxo-8-propyl-4H-1-benzopyran-2-carboxylate

The mixture of isomers from step (d) (6.3 g) was dissolved in dry ethanol (400 ml) and cooled to −60° C. to precipitate the starting materials as a fine solid. The suspension was treated with ozonised oxygen gas at a rate of 25 l/hour for 1 hour with stirring. The reaction mixture, while still at −60° C., was flushed with nitrogen for 15 mins and dimethyl sulphide (2 ml) was added. The reaction mixture was stirred at −10° C. for 1 hour, ice-bath temperature for 1 h and finally room temperature for 1 hour, poured into water, and extracted with ethyl acetate which was washed with water and dried. The solvent was evaporated and the residue recrystallised from ethanol to give 3.8 g of product, mp 137°-138°.

Analysis: Found: C; 62.8% H; 5.4%. $C_{16}H_{16}O_6$ Requires: C; 63.2% H; 5.26%.

(f) Triethyl 2,3-dihydro-3-hydroxy-5-oxo-9-propyl-5H-furo[3,2-g]-[1]-benzopyran-2,2,7-tricarboxylate The product from step (f) (2.6 g), diethyl bromomalonate (2.28 g) and potassium carbonate (1.75 g) were heated under reflux in methyl ethyl ketone (65 ml) with stirring for 0.75 hour. The reaction mixture was cooled, poured into water and extracted with ethyl acetate, which was then washed with brine and dried. The solvent was evaporated and the residue triturated with 30°-40° petroleum ether to give 3.2 g of product. A recrystallisation from aqeuous ethanol gave material, mp 131°-133°.

Analysis: Found: C; 60.0% H; 5.49%. $C_{23}H_{26}O_{10}$ Requires: C; 59.7% H; 5.63%.

(g)

5-Oxo-9-propyl-5H-furo[3,2-g][1]-benzopyran-2,7-dicarboxylic acid

The product of step (f) (2.7 g) was heated under reflux in concentrated hydrochloric acid (20 ml), water (20 ml) and glacial acetic acid (50 ml) for 6 hours with stirring. The reaction mixture was allowed to cool overnight and the solid which had precipitated was collected by filtration. A recrystallisation from glacial acetic acid gave 1.64 g of product, mp 316°-318° dec.

Analysis: Found: C; 58.15% H; 3.8%. $C_{16}H_{12}O_7$ 0.75 $H_2O$ Requires: C; 58.2% H; 3.77%.

(h) Disodium 5-oxo-9-propyl-5H-furo[3,2-g][1]-benzopyran-2,7-dicarboxylate

The product from step (g) (1.0356 g) and sodium bicarbonate (0.528 g) in water (200 ml) were stirred until a clear solution was formed. The solution was filtered and the filtrate freeze-dried to give 1.13 g of pale yellow solid.

Analysis: Found: C; 48.57% H; 2.94%. $C_{16}H_{10}Na_2O_7$ 9.53% water Requires: C; 48.22% H; 3.0%.

EXAMPLE 14
5-Oxo-9-propyl-5H-thieno[3,2-g][1]-benzopyran-2,7-dicarboxylic acid

(a) 0-[4-Acetyl-3-hydroxy-6-(1-propenyl)-2-propylphenyl]-N,N-dimethylthiocarbamate (mixture of E & Z isomers)

E & Z-1-[2,4-Dihydroxy-5-(1-propenyl)-3-propylphenyl] ethanone (19.35 g), potassium carbonate (13.2 g) and dimethylthiocarbamoyl chloride (11.2 g) were heated under reflux in dry acetone (155 ml) for 6 hours. The reaction mixture was cooled, poured into water and extracted into ether, which was washed with brine and then dried. The solvent was evaporated and the residue eluted down a silica gel column using ether/petroleum ether (2:3) as eluant to give the product as 24.8 g of an oily solid.

Analysis: Found: C; 63.54% H; 7.17% N; 4.33% S; 10.1%. $C_{17}H_{23}NO_3S$ Requires: C; 63.6% H; 7.17% N; 4.36% S; 9.97%.

(b) S-[4-Acetyl-3-hydroxy-6-(1-propenyl)-2-propylphenyl]-N,N-dimethylthiocarbamate (mixture of E & Z isomers)

The product of step (a) (5.0 g) was added to diphenyl ether (70 ml) under reflux with stirring. The reaction mixture was heated under reflux with stirring for 5 mins and the excess diphenyl ether evaporated under reduced pressure. The residue was eluted down a silica gel column using ether/petroleum ether (1:1) as eluant to give the sub-title compound, 4.0 g as a viscous oil.

Analysis: Found: C; 63.68% H; 7.35% N; 4.63% S; 9.7%. $C_{17}H_{23}NO_3S$ Requires: C; 63.6% H; 7.17% N; 4.86% S; 9.97%.

(c) S-(4-Acetyl-6-formyl-3-hydroxy-2-propylphenyl)-N,N-dimethylthiocarbamate The product from step (b) (10 g) was dissolved in dry ethanol (500 ml) and cooled to −60°. Ozonised oxygen gas was passed through the solution at a rate of 25.5/hours from an ozonator whilst allowing the temperature to rise to −30° to −40°. The reaction mixture was flushed with nitrogen at −40° and then dimethyl sulphide (3.1 ml) was added. The reaction mixture was stirred at −10° for 1 hour, 0° C. for 1 hour and finally room temperature for 1 hour. The solvent was evaporated to dryness to give a gum which was triturated with 30°-40° C. petroleum ether and cooled to 0° C. to give 7.5 g of solid. A further 1.44 g was obtained by evaporating the petroleum ether washings and eluting the residue down a silica gel column using petroleum ether/ethyl acetate (7:3) as eluant, mp 70°-72° C.

Analysis: Found: C; 58.37% H; 6.46% N; 4.40% S; 10.4%. $C_{15}H_{19}NO_4S$ Requires: C; 58.3% H; 6.15% N; 4.53% S; 10.4%.

(d) Ethyl 5-acetyl-6-hydroxy-7-propylbenzo[b]thiophene-2-carboxylate

The product from step (c) (2 g) and sodium hydroxide (1.3 g) in water (50 ml) were heated at reflux under nitrogen for 2 hours. The reaction mixture was cooled, poured into water, acidified and extracted with ethyl acetate, which was washed well with water and dried. The solvent was evaporated to leave 5-acetyl-4-hydroxy-2-mercapto-3-propyl benzaldehyde (structure confirmed by nmr and ms investigation).

The thiol was dissolved in dry ethyl methyl ketone (30 ml) and potassium carbonate (1.20 g) and diethyl bromomalonate (1.23 ml) added. The reaction mixture was heated under reflux for 0.5 hours under nitrogen. The reaction mixture was then poured into water and extracted with ethyl acetate which was washed with brine twice and dried. The solvent was evaporated to give diethyl 5-acetyl-2,3-dihydro-3,6-dihydroxy-7-propylbenzo[b]thiophene-2,2-dicarboxylate which was confirmed by nmr and ms examination.

The dihydrobenzothiophene was heated under reflux with potassium hydroxide (1.29 g) in ethanol (45 ml) for 15 min. The reaction mixture was poured onto ice, acidified and extracted with ethyl acetate which was washed with water twice, saturated sodium bicarbonate solution twice, then brine and dried. The solvent was evaporated to leave 1.5 g of residue which was eluted down a silica gel column using ether/petroleum ether (3:2) as eluant to give 1.1 g of the sub-title product, mp 88°-91°.

Analysis: Found: C; 62.77% H; 5.98% S; 10.1%. $C_{16}H_{18}O_4S$ Requires: C; 62.7% H; 5.88% S; 10.5%.

(e) Diethyl 5-oxo-9-propyl-5H thieno[3,2-g][1]benzopyran-2,7dicarboxyulate

The product from step (d) (0.5 g) and diethyl oxalate (0.55 ml) dissolved in dry ethanol (10 ml) were added dropwise to sodium (0.15 g) in dry ethanol (20 ml) with stirring. The reaction mixture was heated under reflux and stirred for 1.5 hours, cooled, poured into a mixture of dilute hydrochloric acid and chloroform and the organic layer separated, washed with water and dried. The solvent was evaporated and the residue treated with hydrogen chloride gas in ethanol (30 ml) and heated under reflux for 15 min. The reaction mixture was cooled, poured into water and extracted with ethyl acetate which was washed with water and dried. The solvent was evaporated and the residue eluted through a silica gel pad using ethyl acetate as solvent to give 0.53 g of product which was recrystallised from ethanol to give the sub-title compound (0.34 g) as golden needles, mp 148°-149° C.

Analysis: Found: C; 61.85% H; 5.22%. $C_{20}H_{20}O_6S$ Requires: C; 61.9% H; 5.15%.

(f) 5-Oxo-9-propyl-5H-thieno[3,2-g]benzopyran-2,7-dicarboxylic acid

The product from step (e) (1.9 g, 4.92 mmol) was dissolved in glacial acetic acid (70 ml), treated with concentrated hydrochloric acid (13 ml), water (13 ml) and heated under reflux for 8 hours. The reaction mixture was allowed to cool to room temperature overnight, concentrated hydrochloric acid (10 ml) was added and refluxing continued for 2 hours. The reaction was cooled, poured into water (200 ml) and the product collected by filtration, washed well with water and dried. This crude diacid was treated with sodium bicarbonate (0.9 g) in water (200 ml) and the solution was treated with charcoal, filtered and the filtrate acidified. The gelatinous product was collected by filtration, washed well with water and dried to give 1.45 g (89%) of the title diacid, mp 310° C. dec.

(g) Disodium 5-Oxo-9-propyl-5H-thieno[3,2-g]benzopyran-2,7 dicarboxylate

The product of step (f) (1.0588 g, 3.16 mmol) was added to a solution of sodium bicarbonate (0.531 g, 6.32 mol) in water (100 ml) and stirred until dissolved. The solution was filtered and the filtrate freeze dried to give 1.126 g of disodium salt after drying in vacuum at 80° for 3 hours.

Analysis: calcd. for $C_{16}H_{10}Na_2O_6.21.8\%H_2O$: C, 40.0; H, 4.5; S, 6.68. Found: C, 40.5; H, 4.29; S, 6.59%.

EXAMPLE 15

8-Oxo-4-propyl-8H-furo[2,3-g][1]benzopyran-2,6-dicarboxylic acid

(a) Ethyl 5-hydroxybenzofuran-2-carboxylate

5-Hydroxybenzofuran-2-carboxylic acid (1.1 g) was heated under reflux for 1 hour in ethanol (50 ml) saturated with hydrogen chloride gas. The reaction mixture was cooled, poured into water and extracted with ethyl acetete, which was washed with water and dried over magnesiuym sulphate. The solvent was evaporated and the residue triturated with petroleum ether to give a brown powder, which was treated with ether, filtered from a black tar and the filtrate eluted down a silica gel column using ether as eluant to give 0.78 g of the sub-title ester as a colourless solid mp 110°–112°.

Elemental analysis: Found: C 64.0 H 5.0%. $C_{11}H_{10}O_4$ Required: C 64.1 H 4.85%.

(b) Ethyl 5-(2-propenyloxy)benzofuran-2-carboxylate

The ester from step (a) (9.2 g), anhydrous potassium carbonate (7.43 g) and allyl bromide (6.13 g) were heated under reflux in dry acetone (200 ml) with stirring for 18 hours. The reaction mixture was cooled, poured into water, and extracted with ethyl acetate which was washed with water and dried over magnesium sulphate. The solvent was evaporated to leave a dark oil which was triturated with boiling 40-60 petroleum ether, decanted from a black tar and cooled to less than 0° to give a sticky solid, which was dissolved in ether, washed with 10% sodium hydroxide solution and dried over magnesium sulphate. The solvent was evaporated to give 8.3 g of the sub-title compound as a yellow solid mp 34°–36°.

Elemental analysis Found: C 68.38 H 5.63%. $C_{14}H_{14}O_4$ Required: C 68.29 H 5.69%.

(c) Ethyl 5-hydroxy-4-(2-propenyl)benzofuran-2-carboxylate

The allyl ether from step (b) (1.0 g) was heated at 190°–200° C. for 2 hours under nitrogen. The flask was cooled and the product was powdered in a mortar under petroleum ether (40°–60°) and collection by filtration to give 0.9 g of the sub-title compound, mp 94°–95°.

Elemental analysis: Found: C 68.45 H 5.6%. $C_{14}H_{14}O_4$ Required: C 68.3 H 5.69%.

(d) Ethyl 5-hydroxy-4-propylbenzofuran-2-carboxylate

The propenyl compound from step (c) (6.8 g) was dissolved in dry ethanol (150 ml) and hydrogenated at 45 psi in the presence of 5% palladium on charcoal (0.6 g) until hydrogen uptake had ceased. The catalyst was filtered off, the filtrate evaporated and the residue triturated with petroleum ether to give 5.0 g of the required product mp 99°–101°.

Elemental analysis: Found: C 67.51 H 6.34%. $C_{14}H_{16}O_4$ Required: C 67.7 H 6.45%.

(e) E/Z-2-(2-carboxy-4-propylbenzofuran-5-yloxy)but-2-ene-1,4-dioic acid

The product of step (d) (5.66 g) and dimethyl acetylenedicarboxylate (3.08 ml) were heated under reflux in ethanol (50 ml) with benzyltrimethylammonium hydroxide (a few drops) for 1 hour. The reaction mixture was cooled, sodium hydroxide (5.64 g) in water (50 ml) was added and refluxing continued for 1 hour. The reaction was cooled, dilrted with water, acidified and extracted with ethyl acetate which was washed with water and dried over magnesium sulphate. The solvent was evaporated and the solid residue powdered under petroleum ether (bp 40°–60°), collected by filtration and dried to give 7.3 g of the title compound as a pale yellow powder.

(f) Diethyl 8-oxo-4-propyl-8H-furo[2,3-g][1]benzopyran-2,6-dicarboxylate

The product of step (e) (1.3 g) was heated on the steam bath with stirring in polyphosphoric acid (40 ml) for 1.5 hours. The reaction mixture was poured onto ice and extracted with ethyl acetate, which was washed with water and dried over magnesium sulphate. The solvent was evaporated and the residue treated with ethanol (100 ml) saturated with hydrogen chloride gas and heated under reflux for 2 hours. The reaction mixture was cooled, diluted with water and extracted with ethyl acetate which was washed with water and dried over magnesium sulphate. The solvent was evaporated to leave a sticky solid which was triturated and finally powdered under petroleum ether (bp 40°–60°) to give 0.6 g of the sub-title compound as a pale yellow solid mp 145°–147°.

Elemental analysis: Found: C 64.33 H 5.23%. $C_{20}H_{20}O_7$ Required: C 64.5 H 5.38%.

(g) 8-Oxo-4-propyl-8H-furo[2,3-g][1]benzopyran-2,6-dicarboxylic acid

The diester from step (f) (3.0 g) was heated under reflux in glacial acetic acid (100 ml) and concentrated hydrochloric acid (50 ml) for 16 hours. The reaction mixture was cooled, the insoluble product collected by filtration, washed with ether and dried to give 1.92 g of the title product mp 309°–310° dec.

Elemental analysis: Found: C 60.43 H 3.9%. $C_{16}B_{12}O_7$ Required: C 60.8 H 3.8%.

(h) Disodium 8-oxo-4-propyl-8H-furo[2,3-g][1]benzopyran-2,6-dicarboxylate

The diacid from step (g) (1.84 g) was treated with sodium bicarbonate (0.978 g) in water (80 ml), filtered and the filtrate treated with acetone. A milky precipitate was formed which coagulated on scratching and standing. The di-sodium salt was collected by filtration, redissolved in water (80 ml) and freeze-dried to give 1.89 g of the sub-title compound as a cream coloured powder.

Elemental analysis: Found: C, 45.8; H, 2.39–3.94%. $C_{16}H_{10}Na_2O_7$.14.07% $H_2O$ Required: C,45.87; H, 3.06%.

Thermogravimetric analysis at 200° showed 14.07% water.

EXAMPLE 16

5-Oxo-9-propyl-5H-thieno[3,2-g][1]benzopyran-3,7-dicarboxylic acid

(a) 1-(2-Hydroxy-4-mercapto-3-propylphenyl)ethanone (i) A mixture of 2,4-dihydroxy-3-propylacetophenone (69 g, 355 mmol), anyhydrous potassium carbonate (56 g, 400 mmol) and dimethylthiocarbamoyl chloride (50 g, 400 mmol) in acetone (600 ml) was heated and stirred at reflux for 3 hours. The mixture was cooled and filtered, and the filtrate was evaporated to dryness. The solid obtained was crystallised from ethanol to give the thiocarbamate as colourless prisms, 74.3 g (74%) mp 113°–4°.

(ii) The thiocarbamate (60 g, 213 mmol) from (i) was heated at reflux in diphenyl ether (200 ml) for 5 minutes. The diphenyl ether was removed by distillation and the residue was triturated with ethanol to give the rearranged ester 42.2 g (86%) mp 73.5°.

(iii) To the product of part (ii) (28 g, 100 mmol) in methanol (200 ml) was added a solution of sodium hydroxide (20 g, 500 mmol) in water (100 ml) and the mixture was heated at reflux under nitrogen for 2.5 hours. The reaction mixture was then acidified, and extracted with dichlormethane. The extracts were washed, dried, filtered, and the filtrate was evaporated to dryness leaving an oil which solidified on cooling, to give the sub-title compound, 21 g (100%).

(b) 5-Acetyl-6-hydroxy-7-propylbenzo[b]thiophene-3-carboxylate (i) A solution of the benzenethiol product of step (a) (21 g 100 mmol) in pyridine (100 ml) was stirred and cooled at 0° under nitrogen while ethyl bromopyruvate (19.5 g, 0.10 M) was added dropwise After the addition the mixture was stirred for 30 minutes and was then poured into a larga excess of dil. HCl. The mixture was extracted with chloroform and the extracts were washed well with dil. HCl and water, and were dried (MgSO₄), filtered and the filtrate was evaporated to dryness leaving a red oil, 28 g, (87%).

(ii) The oil from part (i) was heated in polyphosphoric acid (300 ml) at 100° overnight. The reaction was quenched with water, extracted with chloroform and the extracts were washed with aqueous sodium bicarbonate and water, dried (MgSO₄), filtered and the filtrate was evaporated to dryness leaving a brown oil 17.5 g (57% overall). The oil was purified by chromatography on silica eluting with toluene/ethyl acetate 3:1. The oil obtained by evaporation of the eluent solidified on cooling 12 g (39%).

(c) Diethyl 5-oxo-9-propyl-5H-thieno[3,2-g]benzopyran-3,7-dicarboxylate

The ester product of step (b) (6.5 g, 21 mmol) was added to a solution of freshly prepared sodium ethoxide (2.4 g sodium in ethanol 100 ml) and the mixture was stirred at room temperature for 15 minutes. Diethyl oxalate (7.75 g, 55 mmol) was added and the mixture was heated at reflux for 2.5 hours. HCl gas was bubbled through the cooled, stirred mixture after which the mixture was heated at reflux for 1 hour. The resulting mixture was poured into water and extracted with chloroform. The extracts were washed with water, dried (MgSO₄), filtered and the filtrate was evaporated to dryness leaving an oil. This oil was chromatographed on silica eluting with toluene/ethyl acetate (3:1). The solid obtained upon evaporation of the eluant was crystallised from ethanol to give the required diester 1.0 g (12%). mp 142°–3°.

Analysis: Found: C, 61.4; H, 5.25%. $C_{20}H_{20}O_6$ Requires: C, 61.85; H, 5.15%.

(d) 5-Oxo-9-propyl-5H-thieno[3,2-g]benzopyran-3,7-dicarboxylic acid

The product of step (c) (1.0 g, 2.57 mmol) was heated in methanol (20 ml) while N/10 aqueous sodium hydroxide solution (51.55 ml) was added. The mixture was heated at reflux for 2.5 hours. Methanol was removed in vacuo and the aqueous solution was acidified. The solid produced was filtered off, washed well with water and was dried to give the required diacid 0.85 g (100%) mp > 250°.

(e) Disodium 5-Oxo-9-propyl-5H-thieno[3,2-g]benzopyran-3,7-dicarboxylate

The product of step (d) (0.825 g, 2.485 mmol) was added to a solution of sodium hydrogen carbonate (0.4175 g, 4.97 mmol) in water (25 ml). The resulting solution was filtered through a glass filter and freeze-dried. The solid obtained was dried in vacuo to give the disodium salt of the title compound, 0.85 g (93%).

Analysis: Found: C, 43.79; H, 2.3%; S, 7.79%. $C_{16}H_{10}N_aO_6S$ Requires: with 3.5 moles $H_2O$ C, 43.73; H, 2.8%; S, 7.3%.

What we claim is:

1. A benzopyran of formula I

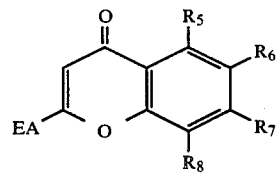

wherein R₆ and R₇ together form the chain —COCH=(A₁E₁)—O— in which 13 0— is attached to R₇,
R₅ represents hydrogen,
R₈ represents propyl,
A represents a single bond,
A₁ represents a single bond, phenylene or $(CH_2)_m$,
m represents an integer from 1 to 10 inclusive, E and $E_1$, which may be the same or different, independently represent —COOH, 5H-tetrazolyl, or $CONR_{24}R_{25}$, wherein $R_{24}$ and $R_{25}$, which may be the same or different, represent hydrogen or alkyl $C_1$ to $C_6$;

provided that when $A_1$ represents a single bond, then $E_1$ represents 5H-tetrazolyl or $CONR_{24}R_{25}$; and pharmaceutically acceptable salts thereof.

2. A benzopyran according to claim 1, wherein

E represents —COOH or a 5H-tetrazolyl group, $E_1$ represents —$CONR_{24}R_{25}$ or a 5H-tetrazolyl group, and pharmaceutically acceptable salts thereof.

3. A benzopyran according to claim 1, which is

10-Propyl-2,8-bis (1H-tetrazol-5-yl)-4H,6H-benzo[1,2-b:5,4-b']dipyran-4,6-dione or 8-(4-Carboxyphenyl)-4,6-dioxo-10-propyl-4H,6H-benzo [1,2-b:5,4-b']diphyran-2-carboxylic acid, and pharmaceutically acceptable salts thereof.

4. A benzopyran according to claim 1, which is 4,6-Dioxo-10-propyl-8-(1H-tetrazol-5yl)-4H,6H-benzo[1,2-b;5,4-b']dipyran-2-carboxylate 8-Aminocarbonyl-4,6dioxo-10-propyl-4H,6H-benzo [1,2-b: 5,4-b']dipyran-2-carboxylic acid, 8-(N,N-Dimethylcarbonylamino)-4,6-dioxo-10-propyl-4H,6H-benzo[1,2-b:5,4-b']dipyran-2-carboxylic acid, 3-(8-Carboxy-4,6-dioxo-10-propyl-4H,6H-benzo[1,2-b:5,4-b']-dipyran-2-) propanoic acid, and pharmaceutically acceptable salts thereof.

5. A pharmaceutical composition which comprises an effective amount of at least one compound according to claim 1 in association with a pharmaceutically acceptable adjuvant, diluent or carrier.

6. A method of treatment of a condition involving an antigen-antibody reaction or excess mucous secretion, which comprises administering an effective amount of a compound according to claim 1.

7. A method according to claim 6, wherein the condition to be treated is asthma.

* * * * *

UNITED STATES PATENT AND TRADEMARK OFFICE
CERTIFICATE OF CORRECTION

PATENT NO. : 4,670,452
DATED      : June 2, 1987
INVENTOR(S) : Kenneth J. Gould & John Louis Suschitzky It is certified that error appears in the above-identified patent and that said Letters Patent is hereby corrected as shown below:

Column 8, line 28, "$(A_{11E})-0-$" should be --$(A_1 E_1)-0$---.

Column 9, line 32, "HC" should be --HCl--.

Column 9, line 50, "2[-di-" should be -- -2,8-di- --.

Column 11, last line, "322°-32 4°" should be --322-4°--.

Column 26, line 26, "dilrted" should be --diluted--.

Column 27, line 37, "42.2 g" should be --42.1 g--.

Column 27, line 54, "dropwise After" should be --dropwise. After--.

Column 27, line 56, "larga" should be --large--.

Column 29, line 19, "diphyran" should be --dipyran--.

Column 30, line 3, "4,6dioxo" should be --4,6-dioxo--.

Signed and Sealed this

Third Day of November, 1987

Attest:

DONALD J. QUIGG

Attesting Officer          Commissioner of Patents and Trademarks